(12) United States Patent
Gross

(10) Patent No.: US 11,458,009 B2
(45) Date of Patent: Oct. 4, 2022

(54) STENT GRAFT SYSTEM AND A METHOD FOR COUPLING STENT GRAFTS AS A STENT GRAFT SYSTEM

(71) Applicant: Christian-Albrechts-Universitaet zu Kiel, Kiel (DE)

(72) Inventor: Justus Gross, Laboe (DE)

(73) Assignee: Universitaet Rostock, Rostock (DE)

( * ) Notice: Subject to any disclaimer, the term of this patent is extended or adjusted under 35 U.S.C. 154(b) by 81 days.

(21) Appl. No.: 16/071,795

(22) PCT Filed: Jan. 20, 2017

(86) PCT No.: PCT/DE2017/100030
§ 371 (c)(1),
(2) Date: Jul. 20, 2018

(87) PCT Pub. No.: WO2017/129167
PCT Pub. Date: Aug. 3, 2017

(65) Prior Publication Data
US 2019/0029799 A1  Jan. 31, 2019

(30) Foreign Application Priority Data
Jan. 25, 2016  (DE) .................... 10 2016 101 273.4

(51) Int. Cl.
*A61F 2/07* (2013.01)
*A61F 2/91* (2013.01)
(Continued)

(52) U.S. Cl.
CPC .................. *A61F 2/07* (2013.01); *A61F 2/91* (2013.01); *A61F 2002/061* (2013.01);
(Continued)

(58) Field of Classification Search
CPC .... A61F 2/07; A61F 2/91; A61F 2/848; A61F 2002/061; A61F 2002/067;
(Continued)

(56) References Cited

U.S. PATENT DOCUMENTS 6,030,414 A * 2/2000 Taheri ...................... A61F 2/07
623/1.1
6,325,826 B1 12/2001 Vardi et al.
(Continued)

FOREIGN PATENT DOCUMENTS

EP    1847237 A1  10/2007
WO   03063729 A2   8/2003
(Continued)

OTHER PUBLICATIONS

International Search Report dated Mar. 5, 2017, in International Application No. PCT/DE2017/100030.

*Primary Examiner* — Jennifer Dieterle
*Assistant Examiner* — Tiffany P Shipmon
(74) *Attorney, Agent, or Firm* — Patent Central LLC; Stephan A. Pendorf

(57) ABSTRACT

A stent graft system (1) with a first stent graft (2) expandable in respect of a diameter, and with at least a second stent graft (3). The first stent graft (2) at least in some areas has a tubular net structure (4) which, in an expanded mode, has a net structure (4) with substantially round annular meshes (5). The at least second stent graft (3) has, at a distal end (6), outwardly extending barbs (7) via which the at least second stent graft (3) can be coupled to the first stent graft (2) in the expanded mode. The distal end (6) of the at least second stent graft (3) passes through a round annular mesh (5) of corresponding diameter and, with its outwardly extending barbs (7), engages on the round annular mesh (5). Also, a method for coupling stent grafts as a stent graft system.

6 Claims, 5 Drawing Sheets

(51) Int. Cl.
*A61F 2/06* (2013.01)
*A61F 2/82* (2013.01)

(52) U.S. Cl.
CPC ... *A61F 2002/067* (2013.01); *A61F 2002/821* (2013.01); *A61F 2220/0083* (2013.01); *A61F 2230/0006* (2013.01); *A61F 2250/006* (2013.01); *A61F 2250/0062* (2013.01)

(58) Field of Classification Search
CPC ...... A61F 2002/8483; A61F 2002/8486; A61F 2/856; A61F 2220/008–222/0016; A61F 2220/0075
See application file for complete search history.

(56) References Cited

U.S. PATENT DOCUMENTS

| | | | |
|---|---|---|---|
| 2006/0085061 A1* | 4/2006 | Vardi | A61F 2/954 623/1.35 |
| 2007/0293940 A1* | 12/2007 | Schaeffer | A61F 2/91 623/1.16 |
| 2008/0119886 A1* | 5/2008 | Greenhalgh | A61B 17/12168 606/200 |
| 2010/0057096 A1* | 3/2010 | Wolf | A61F 2/06 606/108 |
| 2010/0241218 A1 | 9/2010 | Bruszewski et al. | |
| 2013/0204351 A1 | 8/2013 | Cox et al. | |
| 2014/0142509 A1* | 5/2014 | Bonutti | A61B 17/3439 604/164.03 |
| 2014/0180393 A1 | 6/2014 | Roeder | |
| 2014/0350694 A1* | 11/2014 | Behan | A61F 2/966 623/23.65 |

FOREIGN PATENT DOCUMENTS

| | | |
|---|---|---|
| WO | 2005034808 A1 | 4/2005 |
| WO | 2014163957 A1 | 10/2014 |

* cited by examiner

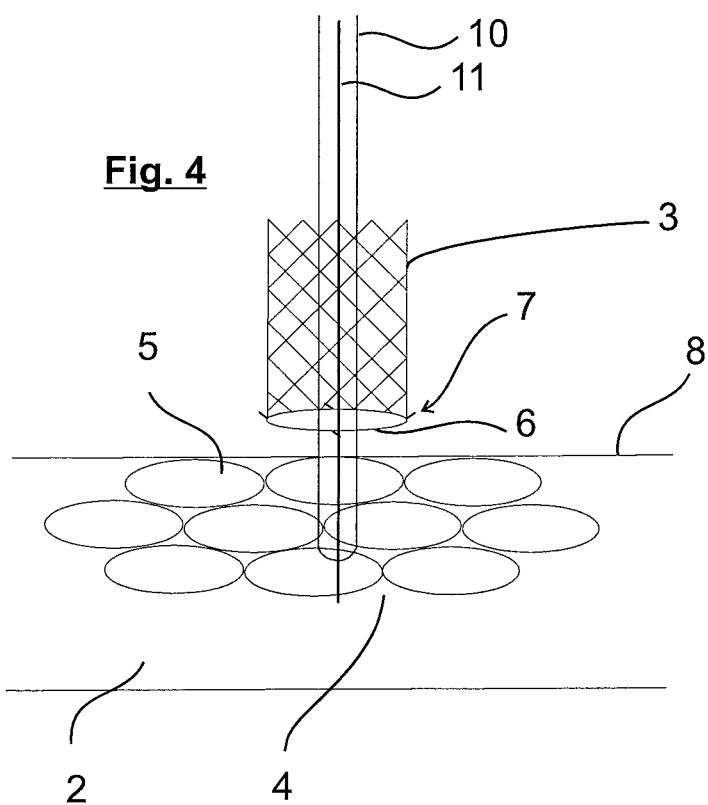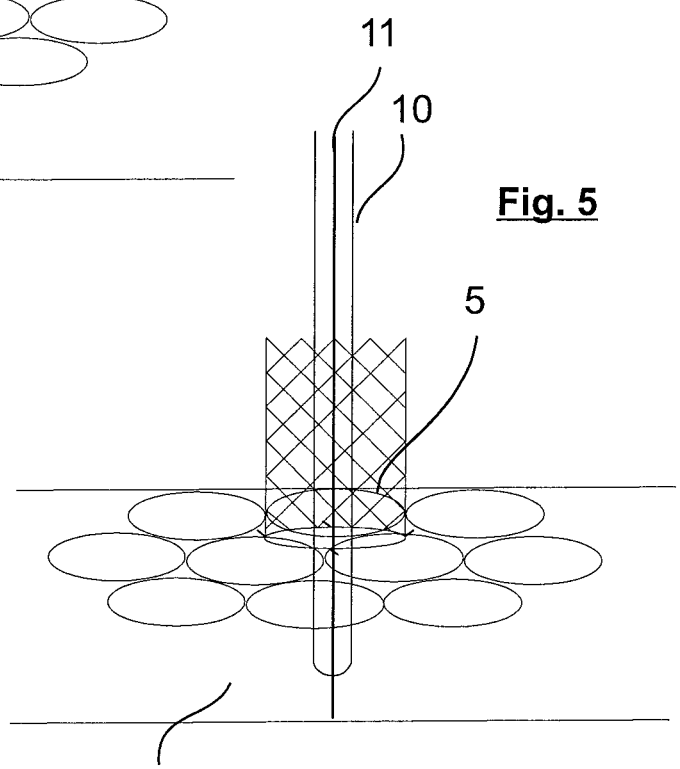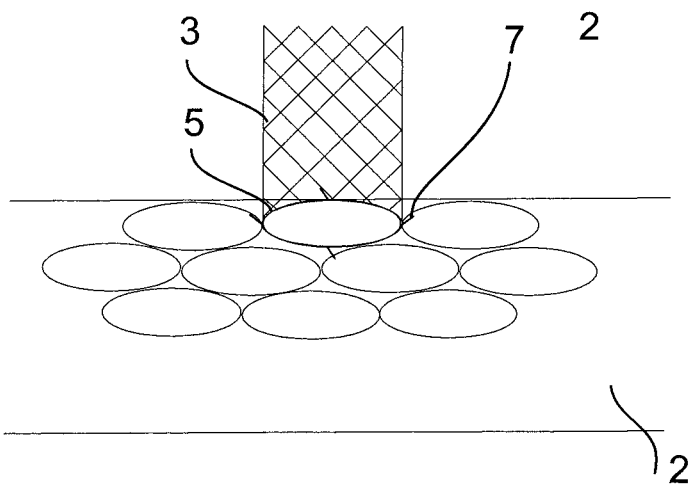

STENT GRAFT SYSTEM AND A METHOD FOR COUPLING STENT GRAFTS AS A STENT GRAFT SYSTEM

The invention relates to a stent graft system comprising a first stent graft expandable in diameter and at least one second stent graft, wherein the first stent graft comprises, at least in regions, a tubular mesh structure having in an expanded mode a mesh structure having substantially circular, annular loops, wherein the at least second stent graft has at a distal end outwardly projecting barbs, via which the at least second stent graft can be coupled to the first stent graft in the expanded mode.

Furthermore, the invention relates to methods for coupling stent grafts as a stent graft system.

In the prior art in classical methods which connect such prostheses to each other, the connection of the stent graft system takes place prior to introduction into the blood vessel. Subsequent changes or adjustments on site are only possible to a very limited extent.

An essential problem in the prior art or a major disadvantage of the currently known respective custom-made systems wherein a complete prosthesis is already assembled before introduction is the finished geometry, which often does not match the actual position of the vessels and vessel junctions.

Also, the deployment process of a prosthesis with a series of branch outlets that are folded and subsequently deployed is disadvantageous in that they can be positioned only to a very limited extent.

The present invention has for its object to provide a stent graft system, which overcomes the problems of the prior art and in particular allows the optimal adaptation on-site, so that an optimal stent graft for the organ can be realized on-site.

This task is solved with a stent graft system according to the main claim and with methods for coupling stent grafts as a stent graft system according to the independent claims.

The stent graft system has a tubular mesh structure with a first stent graft expandable in diameter and at least a second stent graft, wherein the first stent graft has at least in some areas a tubular structure which, in the expanded mode, has a mesh structure having substantially circular, annular loops, wherein the at least one second stent graft has at a distal end outwardly projecting barbs, via which the at least second stent graft can be coupled to the first stent graft in the expanded mode, wherein the at least second stent graft pierces, with the distal end, a circular, annular loop that corresponds to its diameter and engages with the respective outwardly projecting barbs on the circular, annular loop, so that a connection is realized.

In association with the inventive stent graft system, there is understood under the term "ABLE stent" (Arch Branched Laserassisted Endovascular-stent) the construction of an inventive stent graft system with the aid of a laser guided catheter for coupling the system.

The "ABLE-stent" (Arch Branched Laserassisted Endovascular-stent) part of the invention represents a new stent product, with which a new method of endovascular, particularly laser-assisted treatment of arterial blockage pathologies, such as aneurysm and A-dissections, with neuroprotection using heart-lung machine are possible.

The particular characteristics of this invention are:
  complete endovascular repair of the distal ascending aorta, the aortic arch extending down into the aorta descendens;
  via an extracorporeal blood circulation a constant, neuro (embolism) protective circulation of the bds. carotid artery is achieved
  novel ring design in the arch area allows a laser-based, retrograde prosthetic perforation via the aa. brachial and the aa. carotis communis and stent insert
  the ABLE-stent graft under consideration of blood flow to the coronary arteries may also be combined with a minimally invasive aortic flap.

Further, the first stent graft may be coated with a layer, particularly a polymer, such as in particular polytetrafluoroethylene (PTFE). Furthermore, the whole stent graft system may be coated with PTFE.

Further, the material of the mesh structure of the first stent graft can be a shape memory alloy, preferably Nitinol.

In addition, the network structure of the first stent graft may be enmeshed with non-resorbable suture material.

The branched stent diameter can be adjusted to the lumen of the "circles" (lattice structure) with a minimal oversize.

The barbs on the distal ends of the second stent may anchor into a continuous thread coat of the Nitinol braces.

The novelty of the invention of the stent graft is particularly in the lamellar Nitinol network configuration in the area where subsequently the supraaortale branching is to take place. Due to the longitudinal oval form in the area of the ABLE-stent graft as well as the conventional "folding grill"-form of the molding it can elongate under mechanical tugging decrease in maximum cross-sectional diameter, which represents a basic requirement of an endovascular stent-graft system.

The difference is however that after release, that is, shortening of the stent graft, it does not expand with the usual diamond-shape, but rather a circular Nitinol grid. The mathematical/geometric arrangement of the circle configurations then represents the coupling surface to the supraaortic antegrade introduced stent graft branch. In the "branc area", the Nitinol grid is "enmeshed" with non-resorbable suture material, which then becomes the abutment or bearing support for the subsequent branch anchoring.

A corresponding first method according to the invention for coupling the stent graft according to the invention as a stent graft system comprises the steps of:
  inserting the expandable diameter first stent graft in a non-expanded mode into a blood vessel;
  expanding the first stent graft with formation of substantially circular annular loops at least in areas in the mesh structure,
  introducing the at least second stent graft through another blood vessel or a plurality of second stent grafts through one or more further blood vessels, by moving the respective distal end of the respective second stent graft in the direction of the first stent graft, preferably being moved by a respective laser guided catheter,
  piercing a respective substantially circular annular loop in the mesh structure of the first stent graft by a respective distal end of a respective second stent graft,
  coupling the respective distal end to the respective substantially circular annular loop in the mesh structure of the first stent graft by mechanically pulling behind or pulling behind and engaging the barbs in the respective circular annular loop.

A corresponding second method according to the invention for coupling the inventive stent graft as a stent graft system comprises the steps of:
  inserting the expandable diameter first stent graft in a non-expanded state into a blood vessel;

expanding the first stent graft with formation of substantially circular annular loops at least in areas in the mesh structure, introducing the at least second stent graft through another blood vessel or a plurality of second stent grafts through one or more further blood vessels, by moving the respective distal end of the respective second stent graft in the direction of the first stent graft, preferably being moved by a respective laser guided catheter, perforation of the respective layer of the first stent graft by the respective laser guide catheter, piercing, with the respective distal end of the respective second stent graft, a respective substantially circular annular loop in the mesh structure of the first stent graft, coupling the respective distal end to the respective substantially circular annular loop in the mesh structure of the first stent graft by mechanically pulling behind or pulling behind and engaging the barbs into the respective circular annular loop.

A third method according to the invention for coupling according the inventive stent graft as a stent graft system comprises the steps of:

inserting the expandable diameter first stent graft in a non-expanded state into a blood vessel;

expanding the first stent graft with formation of substantially circular annular loops at least in areas in the mesh structure, introducing the at least second stent graft through another blood vessel or a plurality of second stent grafts through one or more further blood vessels, by moving the respective distal end of the respective second stent graft in the direction of the first stent graft, preferably being moved by a respective laser guided catheter, perforation of the respective layer of the first stent graft by the respective laser guide catheter, piercing, with the respective distal end of the respective second stent graft, a respective substantially circular annular loop in the mesh structure of the first stent graft, coupling the respective distal end to the respective substantially circular annular loop in the mesh structure of the first stent graft by mechanically pulling behind or pulling behind and engaging the barbs into the respective annular ring-shaped loop enmeshed with non-resorbable suture material.

In a preferred embodiment of the invention, a laser guiding catheter is used for the positioning of the second stent graft in the stent graft system, which allows in the coupling of the modules of the system, between the first expanded stent graft covered by a layer, and the second stent graft, which must penetrate this layer, to make a laser-based, retrograde prosthesis perforation of the first stent graft, which otherwise occurs mechanically.

In the following an embodiment of the invention will be described in detail with reference to the drawings accompanying the description of the figures, which are intended to illustrate the invention and are not to be considered as limiting:

In the drawings:

FIGS. 4 to 6 show a detail view of the distal end of the second stent graft during the installation process;

FIGS. 1 to 3 show an aortic arch in aortic arch aneurysm/A-dissection with the introduced stent graft system 1 according to the invention.

Figure 1:
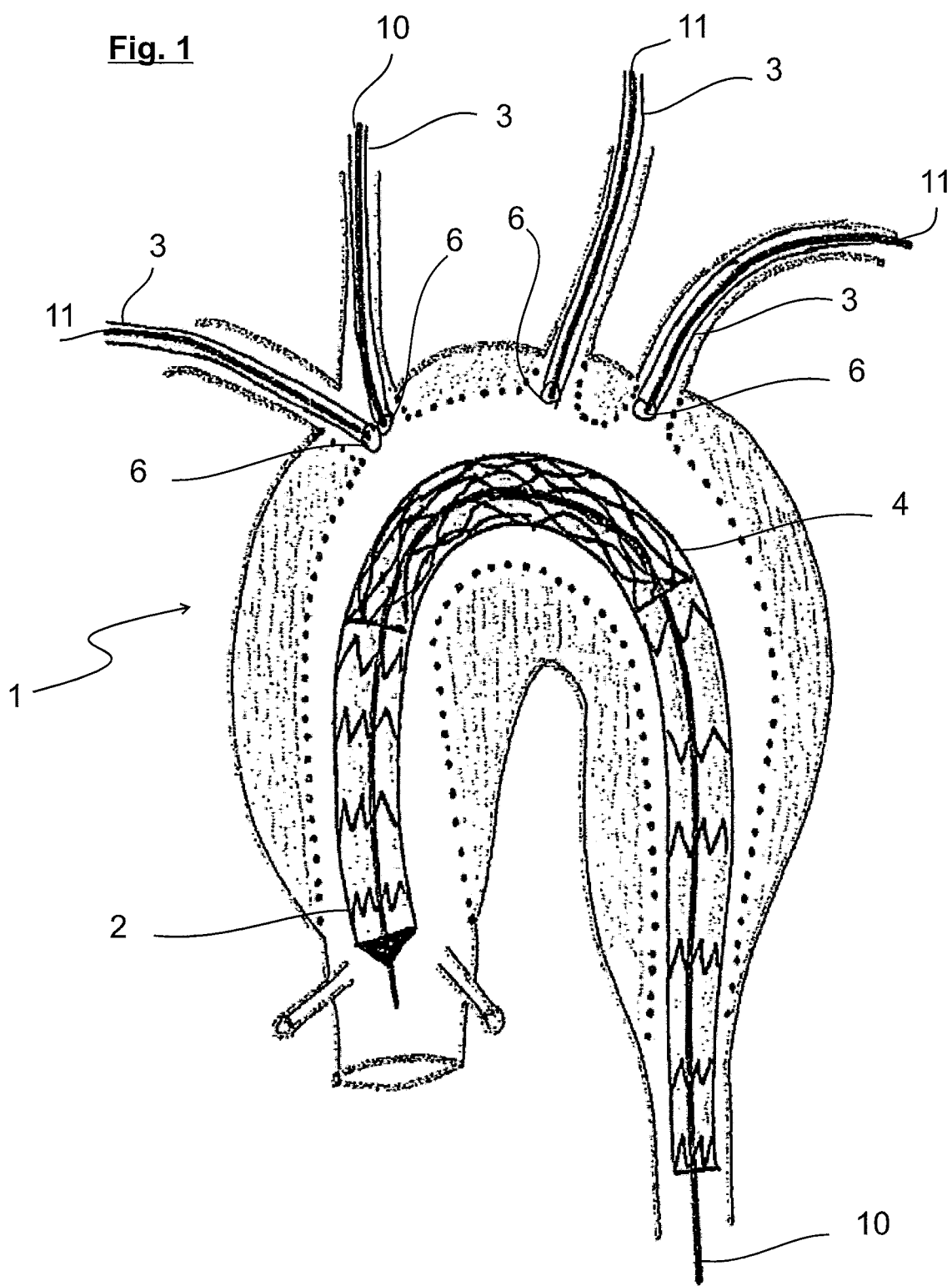
FIGS. 1 to 3 show an inventive stent graft system in the course of installation.

The stent graft system 1 in this embodiment consists of a first stent graft 2 and a second stent graft 3, the first stent graft 2 being inserted into the aortic arch.

Under fluoroscopy in a hybrid OR, the aortic arch is completely displayed on the basis of CT angiography so that work can be done accordingly.

Process steps:

advancing ABLE-stent graft 1 and the laser catheter supraaortal;

bilateral access cervical to the common carotid artery;

bilateral access to the common femoral artery;

installation of an arterio-arterial shunt AFC-ACC bds., if necessary with flow control and extracorporeal circulation pump;

open antegrade positioning system inserted into the ACC bds. and introduction of Terumo guide wire with laser catheter, for example a TurboElite 23 manufactured by Spectranetics, Colorado, USA into the aortic arch under video display control;

puncture and antegrade positioning system insertion into the brachial artery and introduction of Terumo guide wire with laser catheter to the aortic arch under video display control;

open antegrade positioning system insert in the aortic arch unilateral femoral and placement under video display The stent graft system 1 is correspondingly completed by coupling the second stent graft 3 to the first stent graft 2 by hooking the barbs 7 of the second stent graft 3 in the first stent graft 2.

The individual elements of the stent graft system 1 can be found in the corresponding list of reference numerals.

Figure 2:
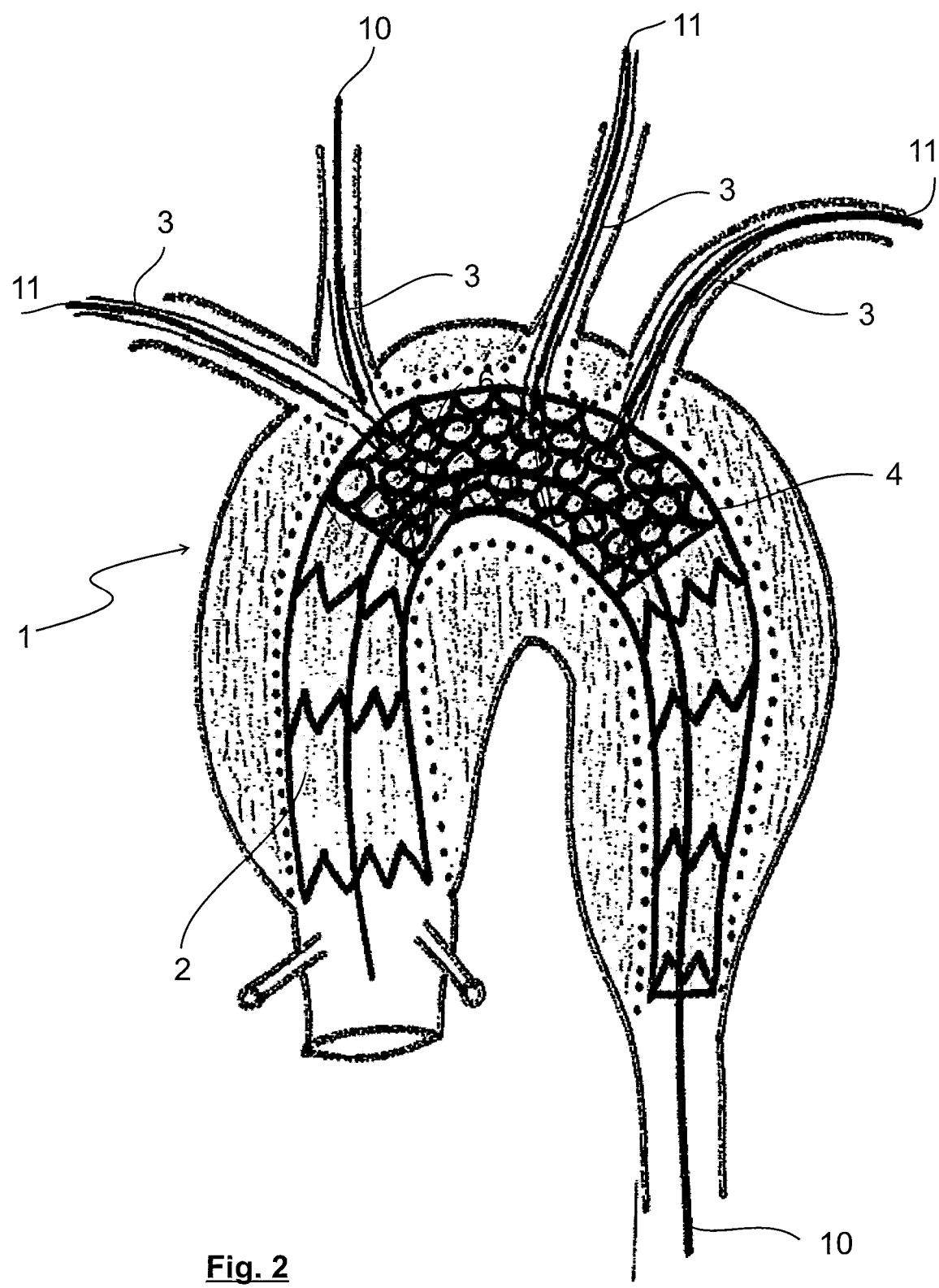

In FIG. 2 is shown:

the deployment of the aortic stent graft, the first stent graft 2, optionally with rapid pacing;

"docking" of the laser catheter to the circular configured "branch" area—the coincidental meeting with a loop 5, for example a Nitinol loop junction, the mesh structure 4 and laser perforation of the PTFE cover of the first stent graft 2 by means of low energy and high repetition rate;

wire presentation in the lumen of the aortic arch.

Figure 3:
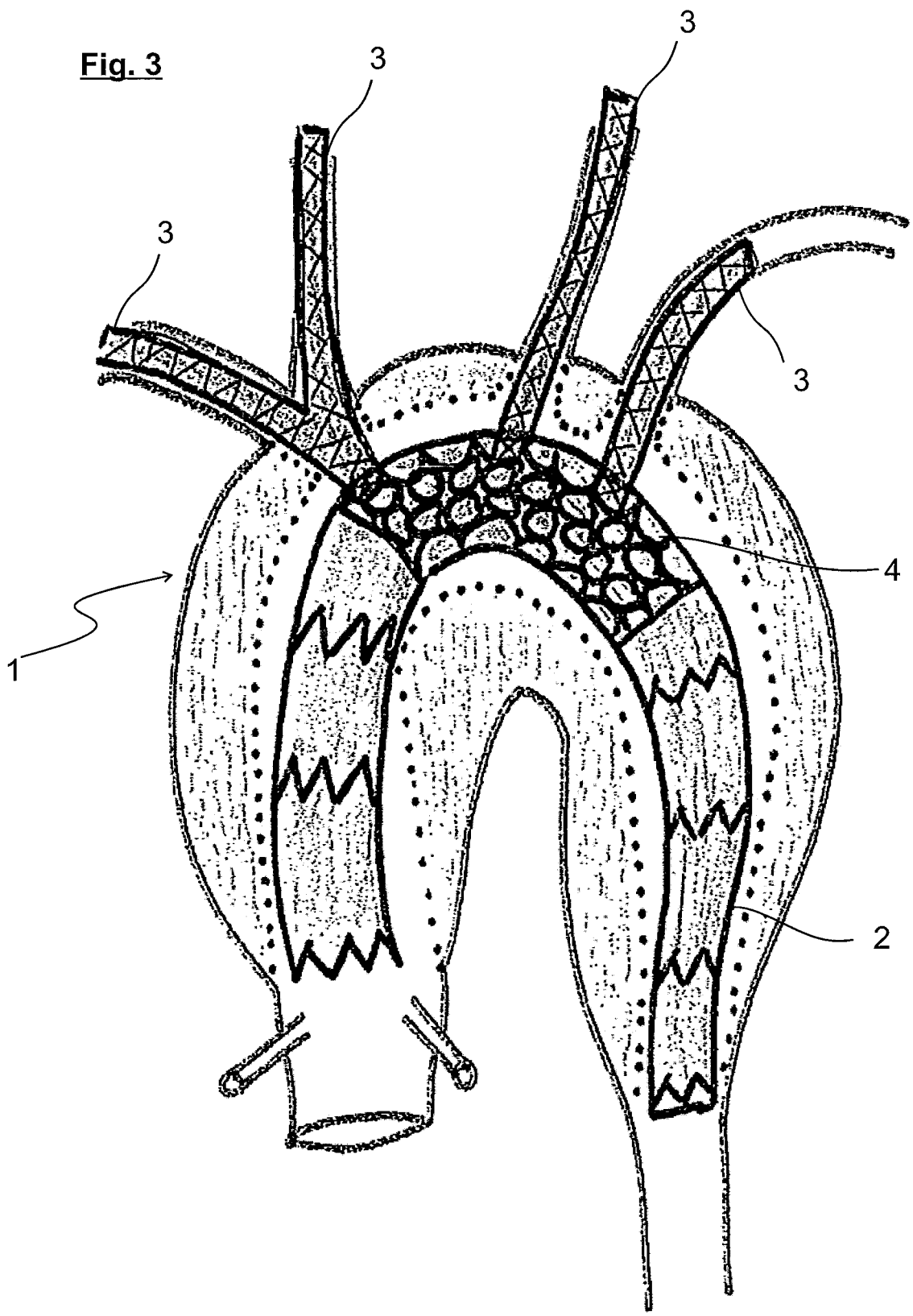

In FIG. 3 the dilatation of the grafts and the completion of the procedure is shown:

dilatation of the stent grafts;

overview angiography;

pulling out of shunt/extracorporeal circulation.

In FIGS. 4 to 6 of the insertion and locking operation of the second stent graft 3 in the first stent graft 2 is shown.

Here, a laser-assisted supra aortic branching occurs. In this case, the application of common branch stents into the 0 and ACC takes place on the left, in the brachiocephalic trunk the implants of an "iliac side branch". The branched stent diameter is adapted to the "circles" of the lumen with minimal oversizing. The barbs 7 on the distal stent ends 6 are anchored in the continuous suture cover of, for example, Nitinol struts.

Figure 7:
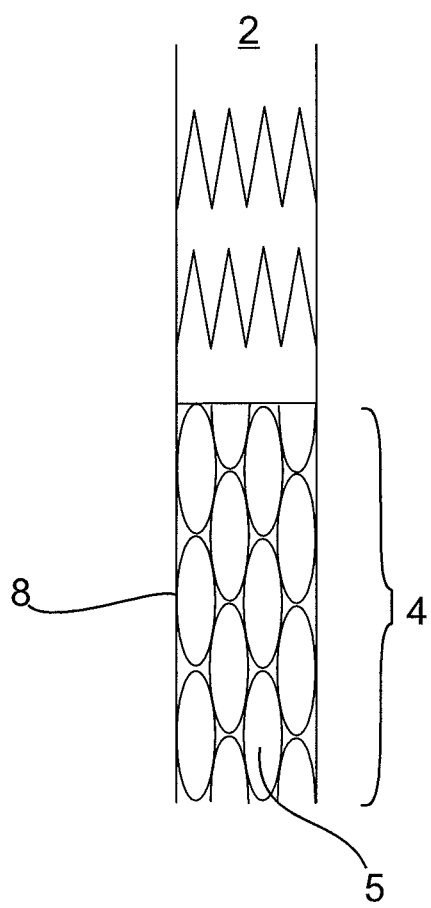
FIGS. 7 and 8 show detail view of the first stent graft before and after the expansion.
Figure 8:
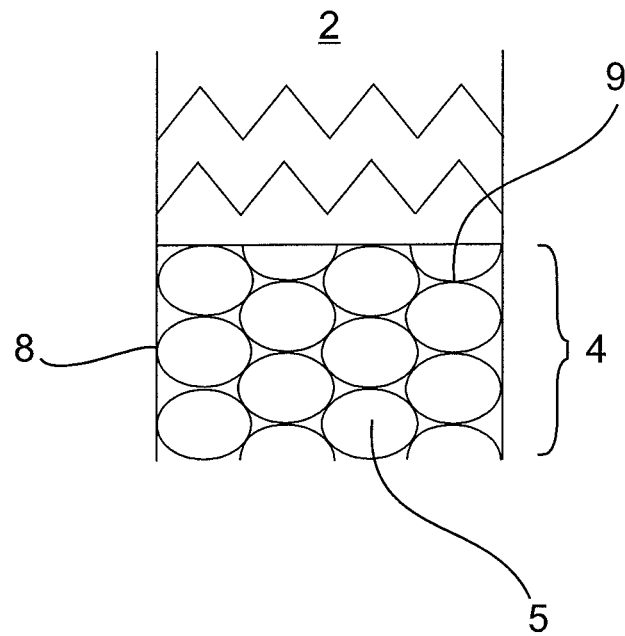

FIGS. 7 and 8 show the first stent graft 2 prior to deployment (FIG. 7) and after deployment (FIG. 8). In the unfolded state, at least circle-like loops 5 are formed, which can be pierced by the second stent graft 3.

LIST OF REFERENCE NUMBERS 1 stent graft system
2 first stent graft 3 second stent graft
4 network structure
5 loop
6 distal end of a second stent graft
7 barb
8 layer
9 suture material
10 guide catheter
11 laser guide catheter

The invention claimed is:

1. A stent graft system having an expandable diameter first stent graft and at least one second stent graft,
the first stent graft comprising a tubular mesh structure having in an expanded mode a loop mesh structure consisting of multiple substantially circular annular loops having the same diameter, wherein the annular loops of the loop mesh structure are arranged around the circumference of the first stent graft such that if the first stent graft were cut axially, most of the annular loops would remain intact,
the at least one second stent graft having a substantially circular distal end having at the substantially circular distal end outwardly projecting barbs, via which the at least one second stent graft is adapted to being coupled to the first stent graft in the expanded mode by piercing with the distal end of the at least one second stent graft through any one of said substantially circular, annular loops of said loop mesh structure such that the respective outwardly projecting barbs engage on the circular annular loop so that a connection is realized.

2. The stent graft system according to claim 1, wherein the first stent graft is coated with a polymer.

3. The stent graft system according to claim 2, wherein a material of the mesh structure of the first stent graft is a shape-memory alloy.

4. The stent graft system according to claim 2, wherein the polymer is polytetrafluoroethylene (PTFE).

5. The stent graft system according to claim 2, wherein a material of the mesh structure of the first stent graft is Nitinol.

6. The stent graft system according to claim 1, wherein the mesh structure of the first stent graft is enmeshed with non-resorbable suture material.

* * * * *